United States Patent [19]
McGinley et al.

[11] Patent Number: 6,018,984
[45] Date of Patent: Feb. 1, 2000

[54] ODOR DETECTING APPARATUS AND METHOD

[76] Inventors: Charles M. McGinley, 13701 30th Street Cir. N., Stillwater, Minn. 55082; John S. Hasslen 3rd, 1033 Manor Pl., Elk River, Minn. 55330

[21] Appl. No.: 09/084,269

[22] Filed: May 26, 1998

[51] Int. Cl.[7] .......................... G01N 31/00; G01N 27/00; A61B 5/00; G01D 21/00
[52] U.S. Cl. ........................ 73/23.34; 73/23.2; 422/83; 422/93
[58] Field of Search .................. 73/23.34, 23.2, 73/23.31; 422/83, 84, 93

[56] References Cited

U.S. PATENT DOCUMENTS

| | | | |
|---|---|---|---|
| 3,618,359 | 11/1971 | Randenbrock et al. | 73/23 |
| 3,882,713 | 5/1975 | Nishida et al. | 73/23 |
| 3,885,550 | 5/1975 | MacLeod | 128/2 R |
| 3,902,851 | 9/1975 | Dravenieks | 23/254 R |
| 4,022,054 | 5/1977 | Biederman | 73/23 |
| 4,036,994 | 7/1977 | Ear | 426/233 |
| 4,457,161 | 7/1984 | Iwanaga et al. | 73/23 |
| 4,496,467 | 1/1985 | Munteanu et al. | 252/92 |
| 4,520,651 | 6/1985 | Litman | 73/23 |
| 4,987,767 | 1/1991 | Corrigan et al. | 73/23.36 |
| 5,627,307 | 5/1997 | Hayashi | 73/23.34 |

*Primary Examiner*—Hezron Williams
*Assistant Examiner*—J. David Wiggins
*Attorney, Agent, or Firm*—Jacobson and Johnson

[57] ABSTRACT

Odors are detected and/or recognized by aspirating samples of odors and odorless air mutually exclusively into an aspirating input of a venturi mixing nozzle along with operating or dilution air and having an assessor or panelist sniff the output of the venturi to determine the presence or absence of odor and to identify an odor, if present. The dilution ratio for each sample tested is changed by feeding the sample odor, or odorless air, to the venturi selectively through branches having different sized restrictive orifices thereby obtaining a wide range of dilution ratios for a particular odor. The different branches are selected by electrically operated solenoid valves which are programmably activated by a programmable logic controller (PLC) as the assessor successively tests each sample. For each sample, the assessor makes three sniffing tests by operating a three position rotary switch before making a selection or decision as to the presence and/or recognition of an odor.

12 Claims, 7 Drawing Sheets

ODOR DETECTING APPARATUS AND METHOD

FIELD OF THE INVENTION

This invention relates to the art of sensing or detecting odors and more particularly toward presenting samples of odors to an assessor or panelist or subject using an olfactometer having a single sample presentation port or mask to convey odor samples having a wide range of dilution ratios.

DESCRIPTION OF THE PRIOR ART

The prior art is best disclosed in U.S. Pat. No. 3,902,851 by Dravnieks titled "METHOD OF DETECTING ODORS AND APPARATUS THEREFORE". The Dravnieks patent discusses the background of the need for providing dilution of the odor samples for testing for the presence of the odors and for identifying and recognizing the odors. For that purpose only, the '851 is incorporated herein by reference. An olfactometer is commonly and conventionally used for the presentation of odors to an assessor or subject. Just to explain, an assessor or panelist is one who is actually making a test of a sample for odors; a subject is an individual or animal being tested for sensitivity to specific odors or to determine a subject's possible use as an assessor or panelist. Hereinafter the term "assessor" or "panelist" will be used with the understanding that it also applies to a "subject". An olfactometer is a dilution apparatus which mixes a sample of the odor in a given ratio with odor-free air for presentation for sniffing by the assessor. There are presently two basic statistical concepts that have been incorporated into the use of olfactometry today. First, there is the "three-alternative forced choice presentation" method or a "triangular forced choice method" wherein each assessor performs odor evaluation by sniffing diluted odor from the olfactometer. Three sample presentations must be sniffed, one of which contains the odor while the other two samples are non-odorous or blanks. The assessor must select one of the three that, in his or her opinion, is different from the other two. Second, the assessor then must declare whether the selection was a guess or an actual detection, i.e., the sample could be readily discriminated from the other two samples, or a recognition, i.e., the sample exhibited a recognizable odor. Then the assessor is presented with three sets of another sample with the odor having a lower dilution ratio; i.e., the odor concentration is greater, and makes the same selections and declarations. After each sample set the assessor advances to the next level of higher concentration odor sample and makes his or her choice with the corresponding acknowledgment as to whether it was a guess, detection or actual recognition. This approach of increasing odor levels of sample presentation is referred to as "ascending concentration series". In practice, ordinarily a machine operator is also present to start the test, to observe the panelist, to check and/or record data, etc.

In the '851 patent each sample set for each dilution level requires a separate set of three sniffing port elements, now usually referred to as presentation ports, so it is clear that the olfactometer of the '851 patent would be limited as to the number of dilution ratios which could be utilized without making the device physically huge in order to produce a large number of dilution ratio samples for testing. Also, for the triangular forced choice method of testing, the '851 patent utilizes three separate sniffing port elements which are physically arranged in a symmetrical pattern as the apexes of an equilateral triangle.

For feeding the odor samples to its sniffing port elements the '851 patent utilizes a peristaltic pump. For changing the dilution ratio, different lengths of flexible tubing are provided to change the volume of the odor sample while the amount of mixing or dilution air is unchanged.

SUMMARY OF THE INVENTION

The present invention utilizes a single presentation port, not three separate ports, for all samples. The presentation port is the output port of a venturi mixing nozzle, oftentimes hereinafter referred to as "venturi" or "venturi valve". The venturi is a constant volume device. Small apertures at the venturi throat are at negative atmospheric pressure brought about by the movement of the operating air and therefore air or odor present at these small apertures will be aspirated into the throat to mix with the venturi operating air. One aspirating input to the venturi mixing nozzle is balancing air and another input is either the odor or odorless air. The odor is carried from a suitable source by a conduit tube or pipe to a first set of solenoid operated valves and odorless air is carried by a conduit tube or pipe to a second set of solenoid operated valves. These two sets of valves feed a manifold which is coupled to an aspirating input of the venturi. These two sets of valves are mutually exclusively operated so that only odorless air or odor in sequential flow streams is allowed to enter the manifold and travel to an aspirating input of the venturi. The conduit from the source of odor, which typically is a conventional bag or other container or odor generator, has a number of different branches each of which is coupled to one of the set of solenoid valves. Each branch has a different sized orifice or restrictor opening for changing the dilution ratio and only one of the multiple branches is selected, by a programmable logic controller (hereinafter referred to as PLC) to pass the odor through its associated valve into the manifold for each sample. The flow of the odorless air to its associated set of valves is similarly branched through restrictor openings and orifices. The balancing air is also carried by a multiple branch conduit with different sized orifices or restrictor openings in each branch with each branch having a separate solonoid valve. Only one of the valves is energized by the PLC to carry the balancing air into its input to the venturi nozzle. This permits a wide variety of ratios of dilution of the odor to be presented to the single output presentation port of the venturi mixing nozzle. The use of multiple branches with different sized orifices to selectively control the dilution ratio produces a uniform and consistent flow at the presentation port so that the assessor does not sense any change in the flow rate at the presentation port to influence his or her decision while testing a wide range of dilution ratios.

For each odor dilution ratio the assessor is presented with three different samples to sniff at the venturi output or presentation port. Two of the samples are odorless air and the third is the diluted odor. In conventional fashion utilizing the three alternative or triangular forced choice method, the assessor must select one of the three as the odor and then indicate whether the selection was a guess, actual detection or recognition. A switching device, preferably a three-position rotary switch, is provided for manual operation by the panelist to present each of the three samples separately for sniffing. The panelist turns the knob successively to three different positions and sniffs the sample. The panelist then turns the knob back to the position he or she has selected as being the one with the odor sample and indicates if this selection was a guess, detection or recognition. Next, the PLC automatically sets the equipment for presentation of the next set of samples to the venturi mixing nozzle for sniffing. As a further feature, to eliminate bias on the part of the panelist, the PLC also automatically randomly resets the location of the switch position at which the next odor sample will appear. Each successive sample of odor is selectively programmed to be of a lower dilution level, i.e., a higher concentration level. By using multiple branches with different sized orifices or restrictors feeding an aspirating input of a single venturi mixing nozzle, virtually an infinite number of odor dilution ratios can be presented while keeping the physical size of the olfactometer well within practical limitations.

DESCRIPTION OF THE PREFERRED EMBODIMENTS

Figure 5:
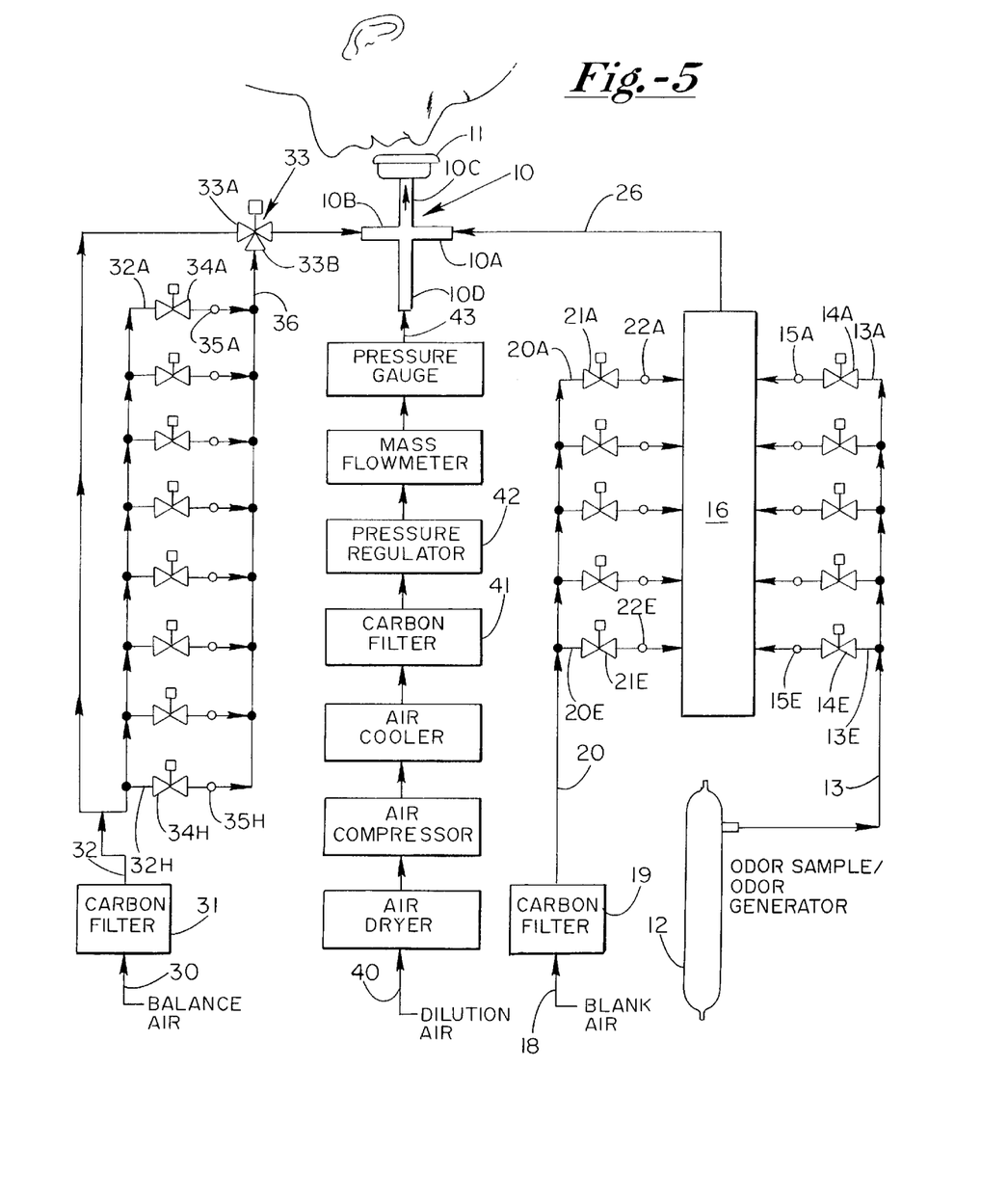
FIG. 5 is a part schematic and partly diagramatic illustration of the air and odor flow paths in a preferred embodiment of the invention.

A venturi mixing nozzle 10 is attached to a presentation mask 11 to make the presentation or output port 10C accessible for sniffing by the assessor. A source of odor 12 which may be a container or other type of odor generator has a conduit or tube 13 for carrying the odor from the source 12. For ease in describing the invention and for illustrative purposes only, with no limitation intended, an example showing an arrangement capable of producing fourteen different odor dilution ratios will be used. Conduit 13 has five different branches designated by reference numerals 13A–E. Each of the branches has an associated electrically controlled solenoid valve 14A–E in series with an associated orifice or restrictor 15A–E with the outputs of the restrictors being fed into a manifold 16. In a similar fashion, blank or odorless air from a suitable source at 18 which is suitably filtered, for example through a purifying filter 19, is carried by a conduit 20 which has five separate branches identified as 20A–E. Each of the branches similarly has an associated electrically controlled solenoid valve 21A–E and an associated restrictor opening or orifice 22A–E with all five branches also connected to manifold 16. The output of manifold 16 is fed to an aspirating input 10A of venturi valve 10 via conduit 26. The input at 10A from manifold 16 will be either diluted odor or blank air.

Odorless balance air from a suitable source 30 is fed through a suitable filter 31 to a conduit 32 and through nine different branches to electrically operated solenoid valve 33. One branch is a direct flow of the balance air in conduit 32 to a first input 33A of solenoid valve 33 and the others are eight different branches identified as 32A–H. Each of the eight branches 32A–H has an associated electrically operated solenoid valve 34A–H which feeds an associated restrictor opening or orifice 35A–H. The outputs of orifices 35A–H feed into a common conduit or pipe 36 which provides a second input at 33B to solenoid valve 33. The output of valve 33 is fed to conduit 37 to provide a second aspirating input at 10B to venturi 10. As mentioned earlier, venturi 10 is attached to mask 11 such that the output or presentation port 10C will be closely adjacent the assessor's nose when the mask is close to the assessor's face.

The venturi operating air from a suitable source 40 is suitably filtered at 41 and is pressure regulated in some conventional fashion at 42 and is fed in conventional fashion into the throat 10D of venturi 10 by conduit 43. The operating air is sometimes referred to as the dilution air because it aspirates the odor or odorless air into the venturi and mixes with and dilutes the odorous air. Balance air 30 is provided because of the nature of the operation of venturi 10. The balance air is not involved in the odor detection process but serves to prevent flow surges and to ensure that there is no detectable or noticeable difference in air flow at the presentation port for each sample which might otherwise influence the panelist's selection.

Figure 1:
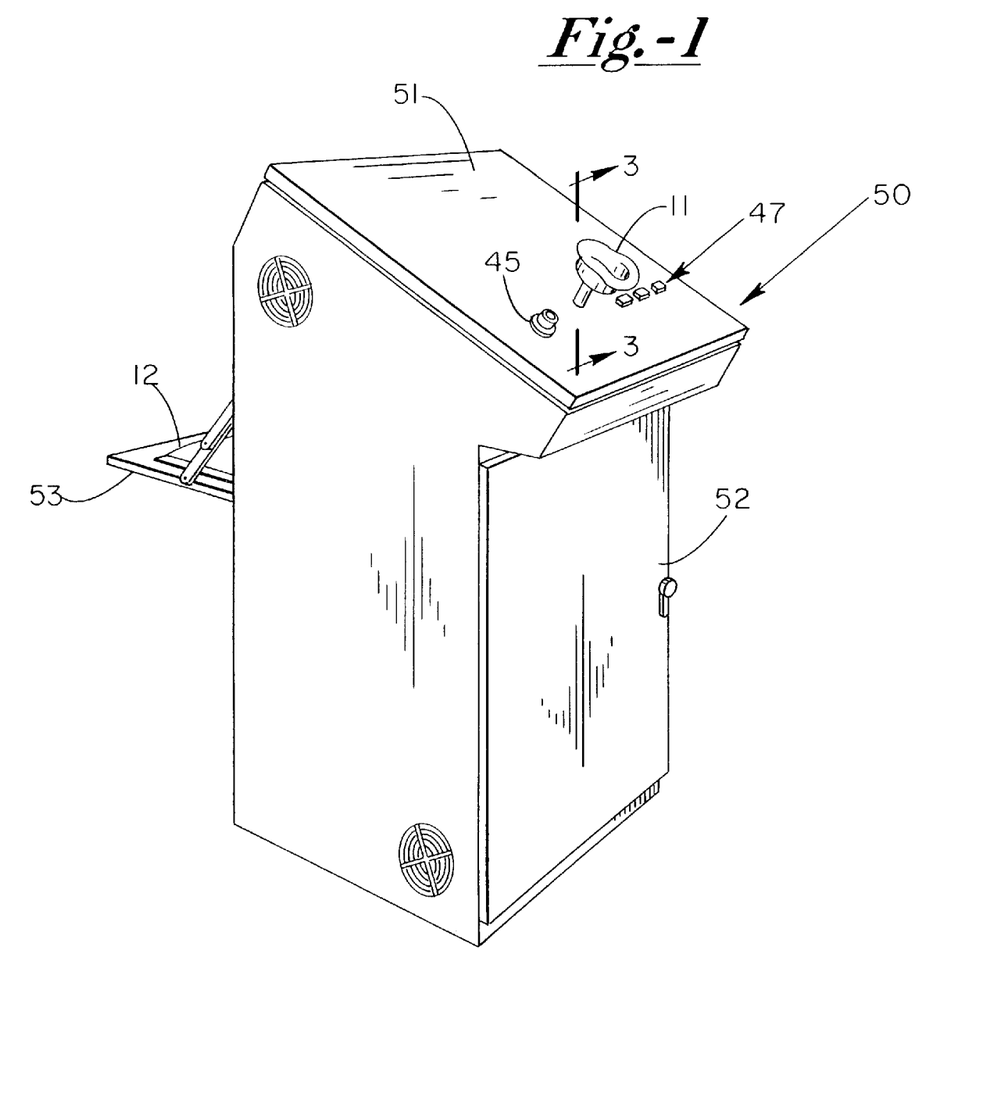
FIG. 1 is a front perspective view of a console utilized in a preferred embodiment of the invention.
Figure 2:
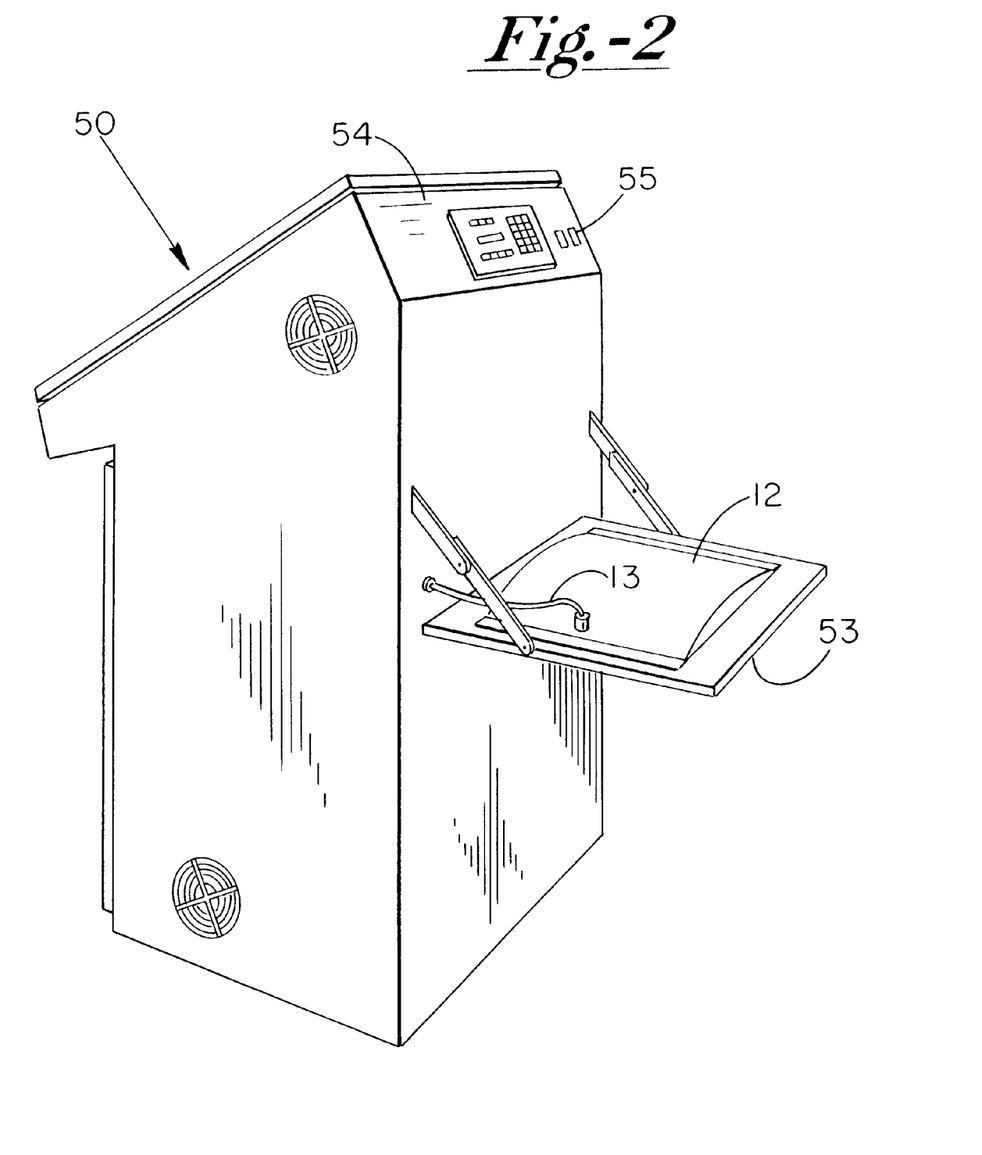
FIG. 2 is a rear perspective view.
Figure 3:
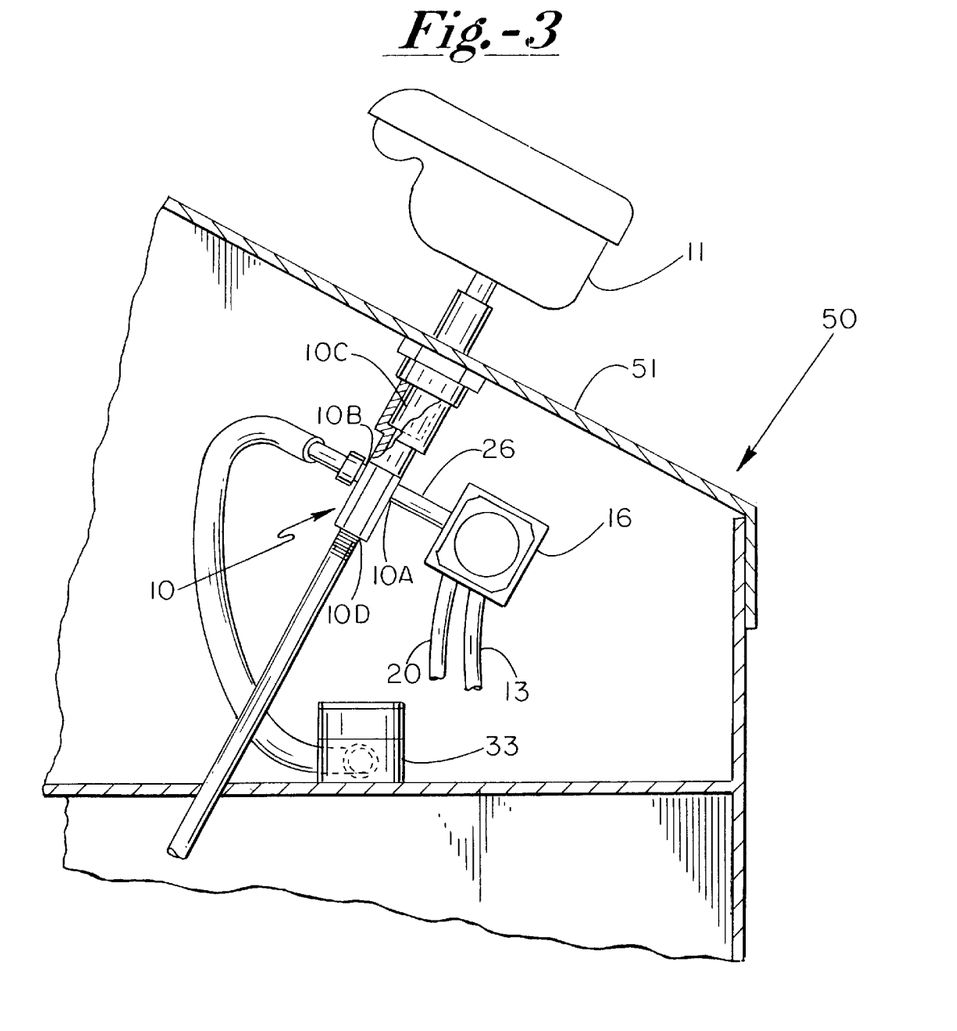
FIG. 3 is a partially sectioned view of the console.
Figure 4:
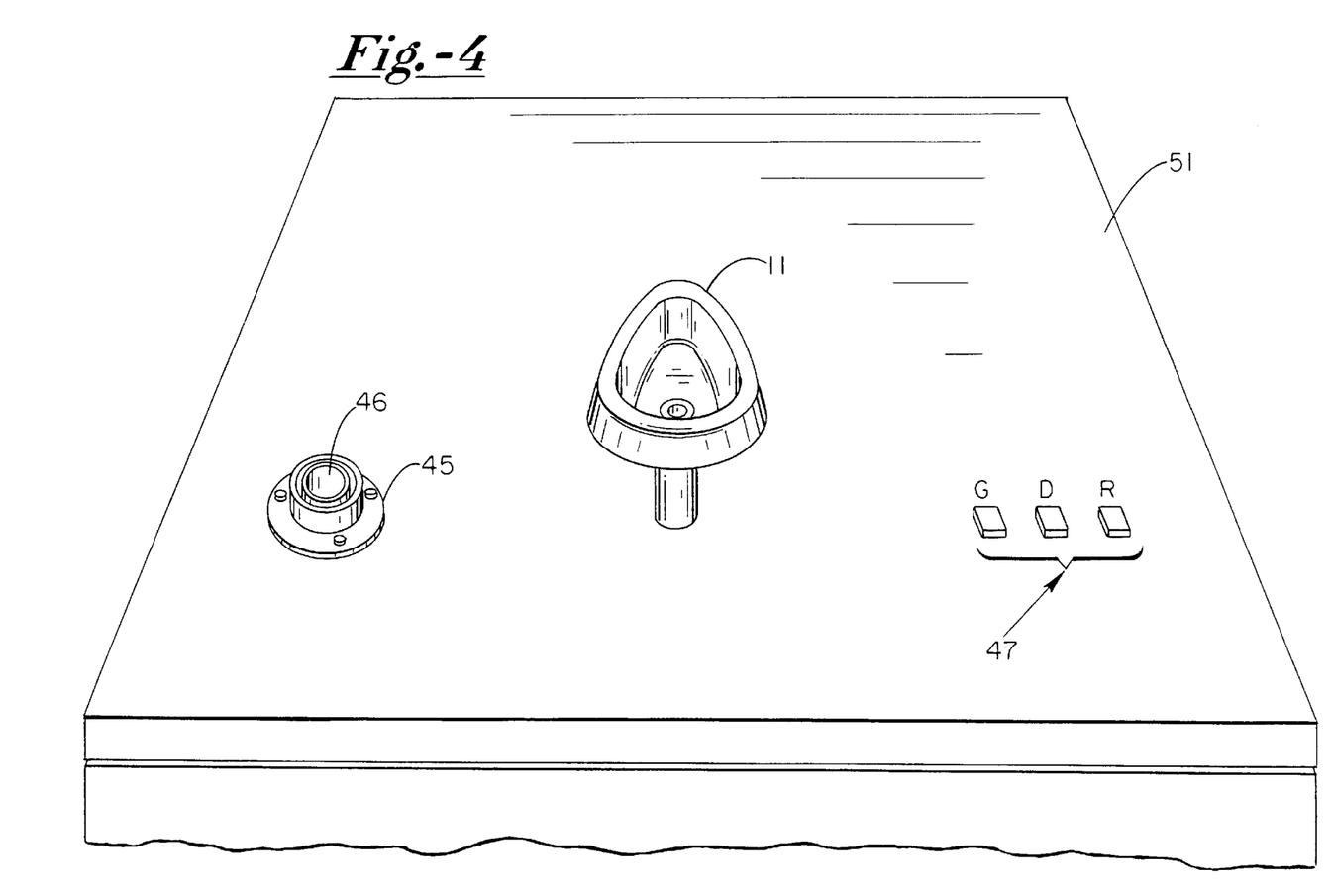
FIG. 4 is a somewhat enlarged view of the front panel on the console utilized by the assessor.

In operation, the assessor turns a rotary electrical switch 45 to one of three positions and presses a "Start" button 46 to initiate the test procedure. The PLC energizes one of the solenoid valves of set 14A–H or of set 21A–H to allow either odorless air or odor to flow to aspirating input 10A of venturi 10 via manifold 16 and conduit 26 and also energizes solenoid 33 to allow balance air into aspirating input 10B. For illustrative purposes only and as a typical example, assume that for a first sample, odor will be presented in the first position of rotary switch 45 and that odorless air is presented in the other two switch positions. Under this assumption, in the first switch position the PLC energizes one of the solenoids 14A–E and solenoid 33 so that balancing air appears at input 10B and a certain volume of odor, determined by the orifice or restrictor 15A–E associated with the selected solenoid 14A–E, appears at aspirating input 10A of venturi 10. A diluted odor in the ratio determined by the size of the selected orifices 15A–E and 34A–H appears at the sniffing output or presentation port 10C. After sufficient time has elapsed for the assessor to sniff the output, the solenoids are deactivated by the PLC so there is no further odor input to the venturi so that only odorless aspirating air flows into and out of venturi 10 from source 40. The assessor then turns rotary switch 45 to its second position and pushes start button 46. The PLC then energizes one of solenoids 21A–E to present odorless air to venturi input 10A and energizes solenoid 33 to provide the same amount of balancing air input at 10B so that the same air flow appears at presentation port 10C. After a suitable sniffing time has elapsed the panelist turns switch 45 to a third position and pushes start button 46 so that the PLC activates one of solenoids 21A–E (which would be the same one as in switch position two) and solenoid 33 so that the same inputs appear at 10A and 10B. At the completion of the three settings, the assessor then turns rotary switch 45 to one of the three positions where he or she thinks the odor sample was present and then indicates by operating one of a set of three switches 47 if the selection was a guess, actual detection, or recognition of the odor.

After a prescribed time to purge the conduits, the venturi and the solenoids of any remnant of any odor, the next sample is ready to be presented. The panelist repeats moving of switch 45 to the three successive positions and sniffs at presentation port 10C for each switch position and makes his or her decision by operating one of switches 47. The respective solenoids 14A–E, 17, 21A–E, 24 and 34A–H and 33 are energized by the PLC so that each successive sample is of a diminished or lower dilution; i.e., each successive sample being a stronger odor sample.

For exemplary and illustrative purposes Table 1 lists fourteen different dilution samples in descending dilution ratios along with corresponding sizes of orifices for the odor 15A–E and for the balancing air 35A–H. Orifices 22A–E for the blank air will be the same sizes as the orifices for the odor. These are shown for illustrative purposes only to illustrate that a wide variety of ratios that can be achieved while still maintaining the same air flow at the presentation port so that the assessor is not influenced by any change in flow rate. The size and number of orifices is a matter of choice depending on the desired number of dilution ratios desired as well as the degree rate of change desired for each successive sample. In the illustrative example, total flow is assumed to be at a rate of 10,000 milliliters per minute. The dilution ratio is the ratio of the total flow (10,000 ml/min.) to the odor flow, i.e., $$\text{Dilution Ratio} = \frac{\text{Total Flow}}{\text{Odor Flow}}.$$

TABLE 1

| Operative Orifice | Size (dia.) (inches) | Operative Orifice | Size (dia.) (inches) | Flow (ml/min) | Dilution Ratio |
| --- | --- | --- | --- | --- | --- |
| 15A | .0015 | 35A | .156 | 0.14 | 71,400 |
| 15B | .0024 | 35A | .156 | 0.30 | 33,300 |
| 15B | .0024 | 35B | .094 | 0.63 | 15,900 |
| 15C | .0028 | 35A | .156 | 1.2 | 08,330 |
| 15C | .0028 | 35B | .095 | 2.4 | 04,170 |
| 15C | .0028 | 35C | .070 | 4.7 | 02,130 |
| 15C | .0028 | 35D | .036 | 9.8 | 01,020 |
| 15C | .0028 | 35E | .015 | 19.6 | 510 |
| 15D | .007 | 35F | .065 | 39.0 | 256 |
| 15D | .007 | 35G | .026 | 76.7 | 130 |
| 15D | .007 | none | none | 152 | 65.8 |
| 15E | .062 | 35B | .094 | 300 | 33.3 |
| 15E | .062 | 35H | .063 | 615 | 16.3 |
| 15E | .062 | none | none | 1152 | 8.68 |

In the chosen example the highest dilution is in the ratio of 10,000 to 0.14 or 71,400 parts of odorless air to one part odor whereas the lowest dilution (highest odor concentration) is in the ratio of 10,000 to 1152 or just over eight parts odorless air to one part odor.

The olfactometer is contained in a console 50 which has a front panel 51 at which the presentation mask 11 is located as well as rotary switch 45 and pushbutton switches 47. As mentioned earlier, a rotary three-position switch is utilized to eliminate or at least minimize bias by the panelist. The switch positions are equally spaced around the knob, i.e., at one-hundred twenty degrees from one another to further eliminate or minimize any bias in the mind of the panelist. Centered on the rotary switch 45 is a pushbutton "Start" switch 46. The selection pushbutton switches 47 respectively identified as "Guess" (G), "Detect" (D) and "Recognize" (R) are also located on front panel 51. Preferably the console 50 has a front door 52 to permit access to the interior of the console which contains the various mechanisms associated with the olfactometer and which have been described above. At the rear of console 50 is a hinged shelf 53 which provides a support for a container 12 for the odor and which has a connection for conduit 13 to carry the odor from the container 12 to the interior of console 50. Also, there is a back panel 54 having some visual presentations which can be used by an overseer or operator to check the data as it is produced by the panelist and/or to make sure that the olfactometer is operating correctly. Of course, all of the data produced by the odor testing would normally also be electronically transmitted or carried to some type of device for recording and/or for further processing. Preferably panel 54 also contains an on/off switch 55 which the operator uses to turn the mechanism on or off as needed.

Figure 6:
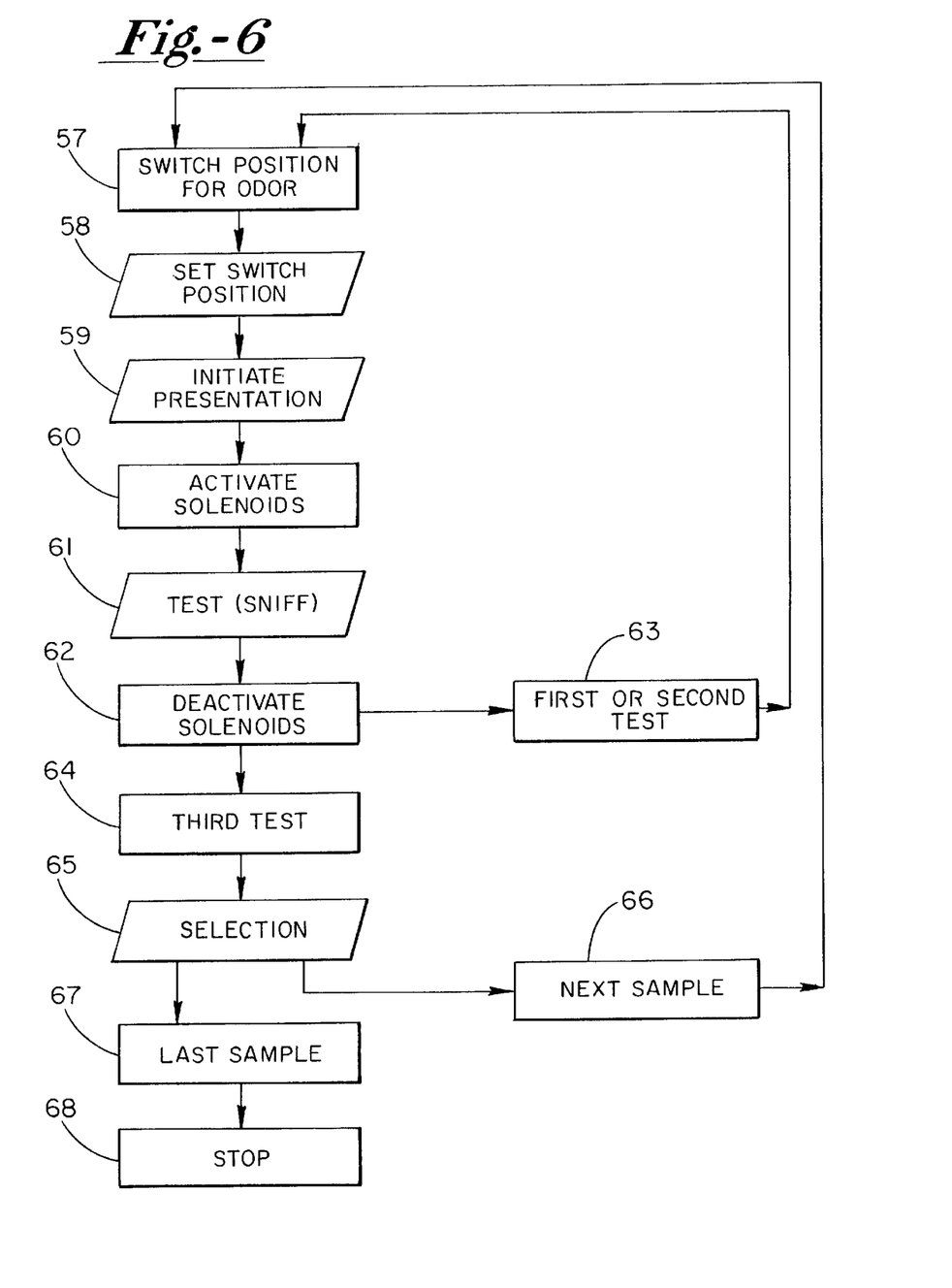
FIG. 6 is a flow chart of the steps in a preferred form of the invention.

FIG. 6 is a flow chart of the functional steps in the operation of the olfactometer by a panelist for a series of odors of different dilution ratios. The steps contained in the rectangular-shaped boxes are those controlled by the PLC and the steps contained in the parallelogram-shaped boxes (not rectangular) are those steps initiated by or performed by the panelist. Initially, as shown at reference numeral 57, the PLC selects one of the three rotary switch positions at which the odor will be presented to presentation or sniffing mask 11. Following that, the panelist at 58 sets rotary switch 45 to a first position and then at 59 pushes start button 46 to initiate the presentation. In response to pushing of button 46, as shown at reference numeral at 60 the PLC activates the suitable solenoids. Virtually at the same time at 61 the panelist tests or sniffs the output at presentation mask 11. This is followed, after a prescribed time, by the PLC deactivating the solenoids at 62. If this is only the first or second test or sample, as shown at box 63, the test is repeated. After the third test 64, reference numeral at 65 selection is made by the panelist by first turning rotary switch 45 to the switch position at which he or she believes the odor was present and then operating one of the switch 47 to indicate whether the selection was a guess (G), an actual detection (D), or an actual recognition (R) of the odor. The PLC then at 66 brings the next sample into play which is the odor with a lesser dilution ratio and all of the steps described above are then repeated for this next sample. After the last sample the PLC at 67 brings the program and the operation to a stop at 68.

Figure 7:
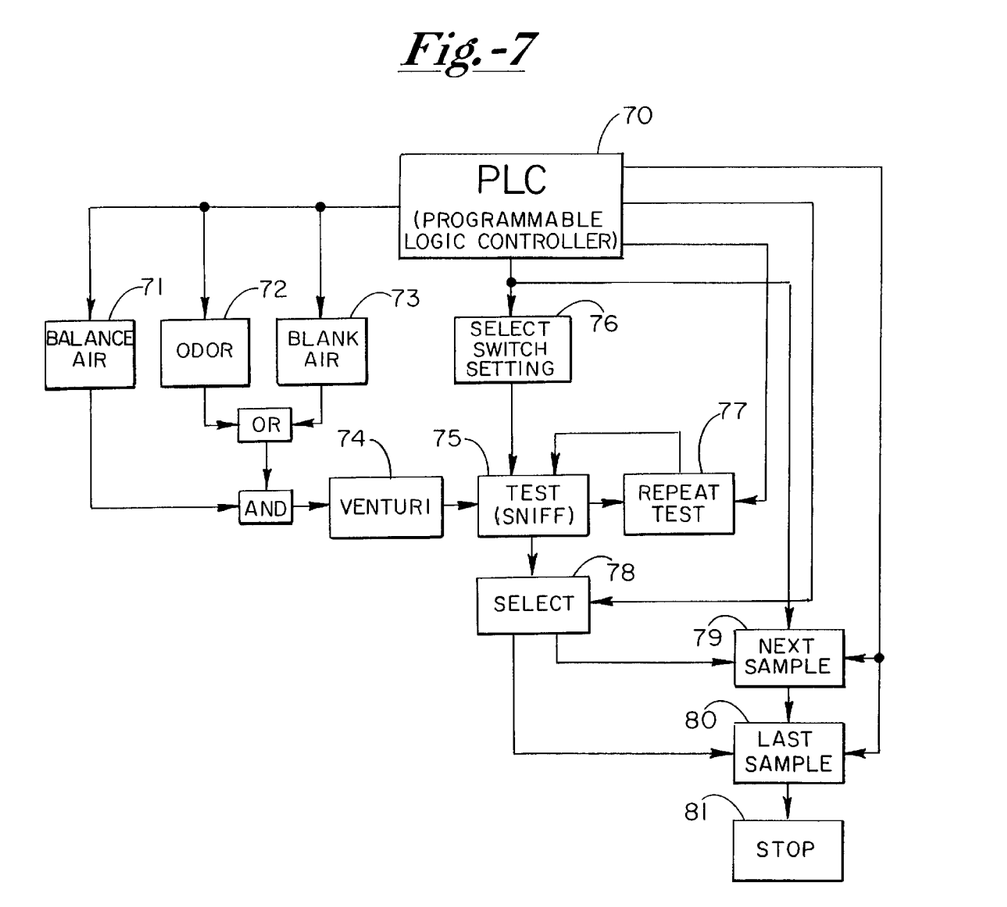
FIG. 7 is a block diagram illustrating the controls in a preferred form of the invention.

FIG. 7 is a combined block diagram and functional illustration of the controlling mechanisms in the olfactometer in the preferred form of the invention. PLC 70 is a commercially available central processing unit (CPU) available from Koyo of Cumming, Ga. It is identified as PLC Series 205 CPU Model 250 and is programmable to operate the various mechanisms by producing the required signals in the necessary timing relationship. It has advance instructions set, memory and power source along with the necessary connectors for making electrical connection with the various component parts. The program conventionally can be altered as necessary in a conventional fashion to produce the various control signals from the PLC as required for the particular application. In other words, software must be provided and communicated or inserted into the PLC for this particular application of making three separate tests by sequential flow streams for each sample odor and identifying the number of tests or samples that are to be tested, etc. PLC 70 operates the balance air solenoids 33 and 34 at block 71, the odor solenoids 14 at block 72 or the blank air solenoids 21 at block 73. The balance air as well as either the odor or the blank air enter venturi valve 10 at block 74 and then are carried to presentation mask 11 for sniffing at box 75. The PLC also makes the selection of which switch setting will have the odor presentation shown by block 76 and controls the repeating of the test at block 77 for each of the three tests run in a given sample. The selection at block 78 under control of the PLC then results in the next sample being presented through block 79. Or if it is the last sample, identified as such at block 80, then the test and entire operation is brought to a halt at block 81.

We claim:

1. A method for detecting an odor comprising the steps of:
   a) feeding separate samples of an odor and odorless air in sequential flow streams mutually exclusively to a first aspirating input of a single-output venturi type mixing nozzle having an output;
   b) feeding odorless air to a second aspirating input of said mixing nozzle;

c) sniffing the output from the mixing nozzle; and d) identifying the output as being an odor or odorless.

2. The method for detecting an odor as described in claim 1 further including a dilution phase of said odor with odorless air as done via the further step of repeatedly changing the dilution of the odor and repeating steps a), c) and d) for each change in extent of odor dilution.

3. The method for detecting an odor as described in claim 2 wherein the odor dilution is successively decreased.

4. A method for detecting an odor using a venturi type mixing nozzle having an aspirating input and a single output, said method involving a dilution phase of said odor with an odorless air, comprising the steps of:

a) feeding to a first aspirating input of a venturi mixing nozzle mutually exclusively one distinct sample of diluted odor and at least one separate sample of odorless air in sequential flow streams;

b) feeding odorless air to a second aspirating input of said mixing nozzle;

c) sniffing the output of the nozzle for each sample; and d) identifying one of the samples as the odor.

5. The method for detecting an odor as described in claim 4 further including the step of:

successively changing the dilution ratio of the diluted odor and then repeating steps a), c) and d) of claim 5 for each change in extent of odor dilution.

6. The method for detecting an odor as described in claim 5 wherein the dilution ratio is successively decreased.

7. Apparatus for detecting odors by sniffing, comprising:

a venturi mixing nozzle having an operating air input, two aspirating inputs and an output port;

a sniffing mask having a presentation port coupled to said venturi output port;

a source of odorless operating air coupled to said venturi operating air input;

a source of odorless balancing air coupled to a first aspirating input;

an odor source;

a conduit having multiple branches coupled to said odor source, said conduit conveying the odor to the other aspirating input;

each of said branches having a separate restrictor for limiting the odor flow; and means for selectively blocking the flow of odor in said branches.

8. The apparatus for detecting odors as described in claim 7 wherein said conduit coupled to said odor source includes a manifold, an output end of each of said branches coupled to said manifold, said manifold in flow communication with said other aspirating input.

9. The apparatus for detecting odors as described in claim 8 wherein said means for blocking the odor flow in said branches comprises:

a set of solenoid operated valves; and control means for selectively energizing said valves.

10. The apparatus for detecting odors as described in claim 9 further including:

a second conduit having multiple branches, said second conduit having an input connected to a source of odorless air and an output coupled to said manifold;

each of the branches of said second conduit having a separate air flow restrictor; and means for selectively stopping the air flow in each branch of said second conduit.

11. The apparatus for detecting odors as described in claim 10 wherein said means for stopping air flow in said second conduit branches comprises:

a second set of solenoid operated valves, said control means selectively energizing said second set of valves.

12. The apparatus for detecting odors as described in claim 9 further including:

a) a third conduit having multiple branches, said third conduit having an input coupled to a source of odorless air and an output coupled to said first aspirating input;

b) each of said third conduit branches having an air flow restrictor; and c) means for selectively stopping the air flow in each branch of said third conduit.

* * * * *